(12) United States Patent
Nakano (10) Patent No.: US 10,532,316 B2
(45) Date of Patent: Jan. 14, 2020

(54) CONCENTRATION COMPUTATION APPARATUS

(71) Applicant: NGK Spark Plug Co., LTD., Nagoya (JP)

(72) Inventor: Yoshihiro Nakano, Komaki (JP)

(73) Assignee: NGK Spark Plug Co., LTD., Nagoya (JP)

( * ) Notice: Subject to any disclaimer, the term of this patent is extended or adjusted under 35 U.S.C. 154(b) by 262 days.

(21) Appl. No.: 15/790,930

(22) Filed: Oct. 23, 2017

(65) Prior Publication Data

US 2018/0126334 A1    May 10, 2018

(30) Foreign Application Priority Data

Nov. 7, 2016   (JP) ................................ 2016-217455

(51) Int. Cl.
| | |
|---|---|
| *B01D 53/94* | (2006.01) |
| *F01N 3/20* | (2006.01) |
| *F01N 13/00* | (2010.01) |
| *G01N 27/407* | (2006.01) |

(52) U.S. Cl.
CPC ......... *B01D 53/9431* (2013.01); *F01N 3/206* (2013.01); *F01N 3/208* (2013.01); *F01N 13/008* (2013.01); *B01D 2258/012* (2013.01); *F01N 2560/021* (2013.01); *G01N 27/4074* (2013.01)

(58) Field of Classification Search
CPC ............ B01D 53/9431; B01D 53/9409; B01D 53/9495; F01N 13/008; F01N 3/208; F01N 3/206; F01N 2560/021; F01N 3/2066; F01N 3/0842; G01N 27/419
See application file for complete search history.

(56) References Cited

U.S. PATENT DOCUMENTS

| | | | | |
|---|---|---|---|---|
| 2015/0013431 | A1* | 1/2015 | Kakimoto | ............ G01N 27/419 73/23.31 |
| 2016/0082390 | A1 | 3/2016 | Nakano et al. | |
| 2019/0011395 | A1* | 1/2019 | Miyamoto | ......... G01N 27/4071 |

FOREIGN PATENT DOCUMENTS

JP    2016-65862 A    4/2016

* cited by examiner

*Primary Examiner* — David Z Huang
(74) *Attorney, Agent, or Firm* — Leason Ellis LLP (57) ABSTRACT

A microcomputer acquires first and second $NH_3$ electromotive forces from a first $NH_3$ detection section and a second $NH_3$ detection section, and computes a $NH_3$ concentration, which is the concentration of $NH_3$ contained in exhaust gas. The first and second $NH_3$ detection sections output the first and second $NH_3$ electromotive forces which vary with both the concentrations of $NH_3$ and a flammable gas contained in the exhaust gas. The microcomputer acquires a second pumping current from an NOx detection section and computes an NOx concentration, which is the concentration of NOx contained in the exhaust gas. The NOx detection section outputs the second pumping current which varies with the concentration of NOx and the concentration of $NH_3$. The microcomputer determines whether or not the exhaust gas contains the flammable gas based on at least the first and second $NH_3$ electromotive forces and the second pumping current.

6 Claims, 5 Drawing Sheets

CONCENTRATION COMPUTATION APPARATUS

This application claims the benefit of Japanese Patent Application No. 2016-217455, filed Nov. 7, 2016, which is incorporated herein by reference in its entirety.

FIELD OF THE INVENTION

The present disclosure relates to a concentration computation apparatus for computing the concentration of ammonia.

BACKGROUND OF THE INVENTION

As disclosed in Japanese Patent Application Laid-Open (kokai) No. 2016-65862, there has been known a technique of determining that a rich spike has occurred when the concentration of oxygen contained in exhaust gas decreases sharply.

Problems to be Solved by the Invention

However, in some cases, even when a rich spike occurs, the concentration of oxygen contained in exhaust gas does not decrease sharply.

It is an object of the present disclosure to improve the accuracy in detecting the rich spike.

SUMMARY OF THE INVENTION

Means for Solving the Problems

One aspect of the present disclosure provides a concentration computation apparatus which computes the concentration of ammonia contained in a measurement gas and which comprises a first computation section, a second computation section, a flammable gas determination section, a concentration setting section, and a setting prohibition section.

The first computation section is configured to acquire a first concentration signal which is output from a first detection section and whose value varies with both the concentration of ammonia contained in the measurement gas and the concentration of a flammable gas contained in the measurement gas. The first computation section is configured to compute a first computed concentration, which is the concentration of ammonia contained in the measurement gas, based on the first concentration signal.

The second computation section is configured to acquire a second concentration signal which is output from a second detection section, whose value varies with the concentration of a specific gas other than ammonia and the flammable gas contained in the measurement gas, and also varies with one of the concentration of ammonia contained in the measurement gas and the concentration of the flammable gas contained in the measurement gas. The second computation section is configured to compute a second computed concentration, which is the concentration of the specific gas, based on the second concentration signal.

The flammable gas determination section is configured to determine whether or not the measurement gas contains the flammable gas based on at least the first concentration signal and the second concentration signal.

The concentration setting section is configured to set the first computed concentration as a latest ammonia concentration when the flammable gas determination section determines that the measurement gas does not contain the flammable gas.

The setting prohibition section is configured to prohibit the concentration setting section from setting the first computed concentration as the latest ammonia concentration when the flammable gas determination section determines that the measurement gas contains the flammable gas.

The concentration computation apparatus of the present disclosure configured as described above determines whether or not the measurement gas contains the flammable gas based on the first concentration signal and the second concentration signal. The value of the first concentration signal varies with both the concentrations of ammonia and the flammable gas contained in the measurement gas. The value of the second concentration signal varies with one of the concentrations of ammonia and the flammable gas.

Specifically, in the concentration computation apparatus of the present disclosure, the second detection section may output the second concentration signal whose value varies with the concentration of ammonia. In this case, when the output value of the second concentration signal is smaller than the output value of the first concentration signal, the measurement gas can be determined to contain the flammable gas. This is because, although the first detection section outputs the signal whose value varies with the concentration of the flammable gas, the second detection section does not output the signal whose value varies with the concentration of the flammable gas.

In this sensor controller, the second detection section may output the second concentration signal whose value varies with the concentration of the flammable gas. In this case, when the output value of the second concentration signal is larger, the measurement gas can be determined to contain the flammable gas. This is because the second detection section outputs the signal whose value varies with the concentration of the flammable gas.

As described above, the concentration computation apparatus of the present disclosure can determine whether or not the measurement gas contains the flammable gas. When a rich spike occurs, the flammable gas is contained in the measurement gas. Therefore, the concentration computation apparatus of the present disclosure can detect the rich spike even when the concentration of oxygen contained in the measurement gas does not decrease sharply, so that the accuracy in detecting the rich spike can be improved.

The concentration computation apparatus of the present disclosure prohibits the concentration setting section from setting the first computed concentration as the latest ammonia concentration when the flammable gas determination section determines that the measurement gas contains the flammable gas. Therefore, the concentration computation apparatus of the present disclosure can prevent a reduction in the accuracy of computation of the ammonia concentration when a rich spike occurs, even in the case where the first detection section outputs the first concentration signal whose value varies with both the concentration of ammonia and the concentration of the flammable gas.

In the one aspect of the present disclosure, the flammable gas determination section may determine whether or not the measurement gas contains the flammable gas when a change in the first computed concentration in a predetermined first time interval is greater than a predetermined start determination value.

In this case, the concentration computation apparatus of the present disclosure can prevent occurrence of a situation in which the determination by the flammable gas determination section is performed even when the first computed concentration varies slightly due to noise. Thus, the processing load of the concentration computation apparatus can be reduced.

In the one aspect of the present disclosure, the second detection section may detect nitrogen oxide as the specific gas and output the second concentration signal whose value varies with the concentration of ammonia contained in the measurement gas. In this case, the concentration computation apparatus of the present disclosure can be used for computation of the concentration of nitrogen oxide in a system for cleaning nitrogen oxide contained in exhaust gas discharged from an internal combustion engine.

In the one aspect of the present disclosure, the flammable gas determination section may determine whether or not the measurement gas contains the flammable gas through use of a predetermined first concentration parameter to have a positive correlation with the output value of the first concentration signal and a predetermined second concentration parameter to have a positive correlation with the output value of the second concentration signal, wherein the flammable gas determination section determines that the measurement gas contains the flammable gas when a change in the first concentration parameter in a predetermined first time interval is greater than a change in the second concentration parameter in a predetermined second time interval.

In this case, since the concentration computation apparatus of the present disclosure uses changes in the first and second concentration parameters for the determination, as compared with the case where an absolute value is used, the influences of the concentrations of ammonia and the specific gas present as an atmospheric reference can be reduced, whereby more accurate determination becomes possible.

In the one aspect of the present disclosure, preferably, the second time interval differs from the first time interval. Specifically, the first and second time intervals are determined in accordance with the time required for the concentration signal output from each detection section to change with a change in the specific gas. For example, in the case where the second detection section detects nitrogen oxide as the specific gas and the time required for the value of the second concentration signal to change with a change in the specific gas in the measurement gas is longer than the time required for the value of the first concentration signal to change with a change in the flammable gas in the measurement gas, it is preferred to render the second time interval longer than the first time interval. The time required for the concentration signal output from each detection section to change with a change in the specific gas differs depending on the position and characteristics of each detection section. As a result, the concentration computation apparatus of the present disclosure can prevent occurrence of a situation in which the magnitude of the change in the second computed concentration which corresponds to a change in the concentration of nitrogen oxide in the measurement gas is computed such that the computed magnitude is smaller than the actual magnitude.

In the one aspect of the present disclosure, the concentration computation apparatus of the present disclosure further comprises an integral gas sensor that contains the first detection section and the second detection section. In this case, the concentration computation apparatus can detect the ammonia concentration and the nitrogen oxide concentration in regions of the measurement gas which are approximately the same.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

An embodiment of the present disclosure will be described with reference to the drawings.

A multi-gas detection apparatus of the present embodiment is used for a system which is mounted on a vehicle and in which an SCR (selective catalytic reduction) catalyst for cleaning nitrogen oxide contained in exhaust gas discharged from an internal combustion engine is disposed and urea is supplied to the SCR catalyst as a reducing agent. The system includes an NOx storage reduction catalyst, a diesel oxidation catalyst (DOC), and/or a diesel particulate filter (DPF), and a so-called rich spike is performed for cleaning these catalysts. More specifically, the multi-gas detection apparatus detects the concentrations of ammonia, nitrogen dioxide, and nitrogen oxide contained in the exhaust gas on the downstream side of the NOx storage reduction catalyst or the SCR catalyst. The vehicle on which the multi-gas detection apparatus is mounted is referred to as the "present vehicle." Ammonia, nitrogen dioxide, and nitrogen oxide are denoted as $NH_3$, $NO_2$, and NOx, respectively.

Figure 1:
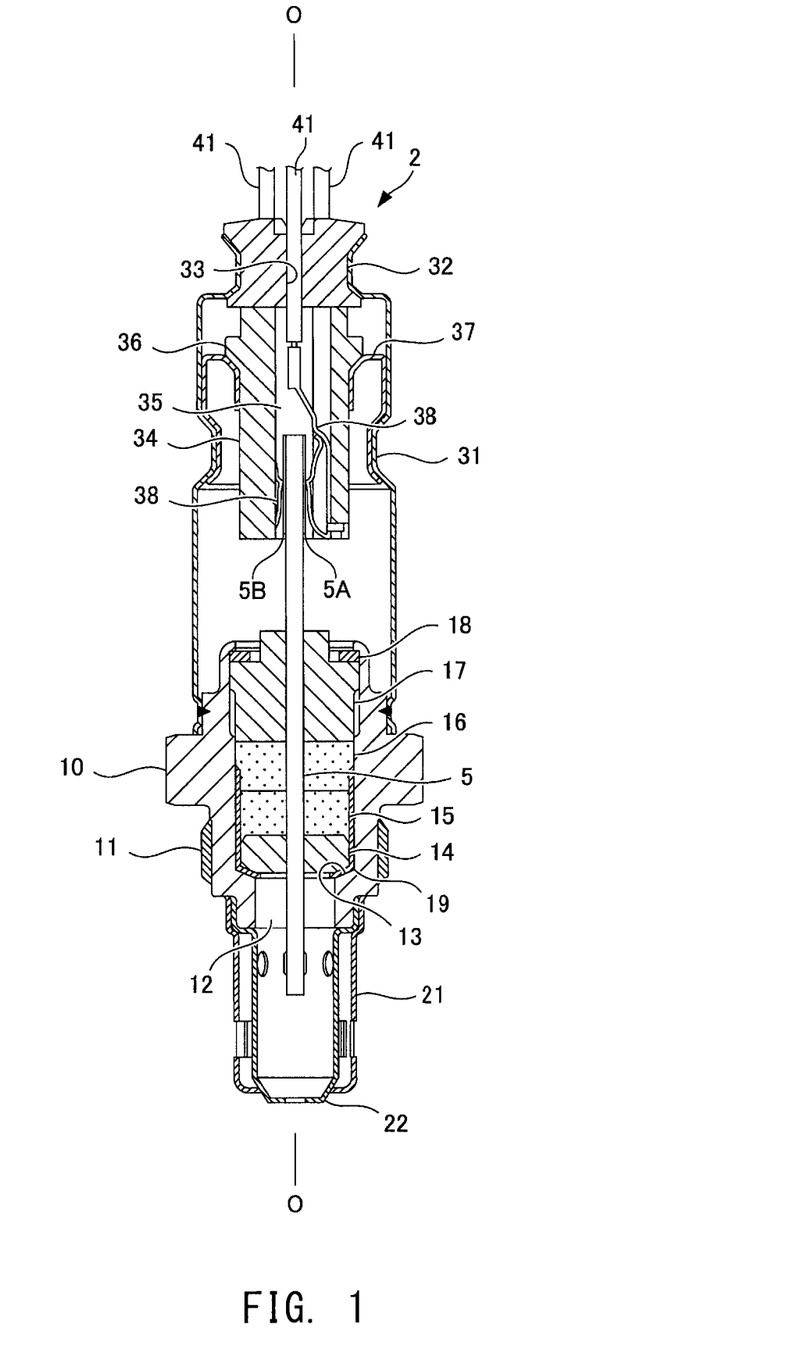
FIG. 1 is a cross-sectional view showing the internal structure of a multi-gas sensor 2.
Figure 2:
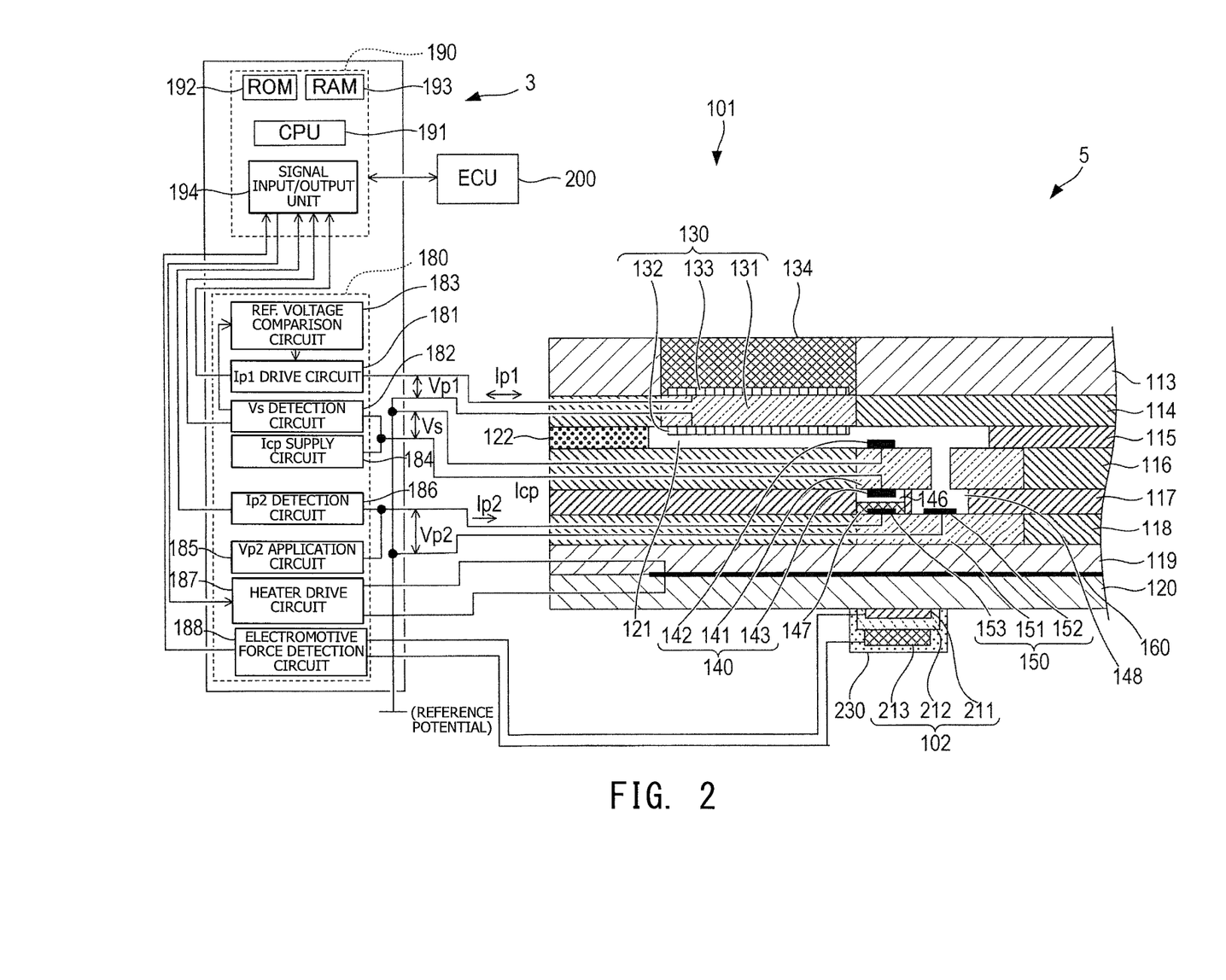
FIG. 2 is an illustration showing the schematic structures of a sensor element unit 5 and a control section 3.

The multi-gas detection apparatus includes a multi-gas sensor 2 shown in FIG. 1 and a control unit 3 shown in FIG. 2.

As shown in FIG. 1, the multi-gas sensor 2 includes a sensor element unit 5, a metallic shell 10, a separator 34, and connection terminals 38. In the following description, the side of the multi-gas sensor 2 on which the sensor element unit 5 is disposed (i.e., the lower side in FIG. 1) is referred to as a forward end side, and the side on which the connection terminals 38 are disposed (i.e., the upper side in FIG. 1) is referred to as a rear end side.

The sensor element unit 5 has a plate shape extending in the direction of an axial line O. Electrode terminal portions 5A and 5B are disposed at the rear end of the sensor element unit 5. In FIG. 1, only the electrode terminal portions 5A and 5B are shown as electrode terminal portions formed in the sensor element unit 5 for the purpose of simplifying the drawing. However, in actuality, a plurality of electrode terminal portions are formed according to the number of, for example, electrodes included in an NOx detection section 101, a first ammonia detection section 102, and a second ammonia detection section 103 described later.

The metallic shell 10 is a tubular member, and a threaded portion 11 used to fix the multi-gas sensor 2 to an exhaust pipe of an internal combustion engine is formed on the external surface of the metallic shell 10. The metallic shell 10 has a through hole 12 extending in the direction of the axial line O and a ledge 13 protruding inward in the radial direction of the through hole 12. The ledge 13 is formed as an inward tapered surface extending from the radially outer side of the through hole 12 toward its center and inclined toward the forward end side.

The metallic shell 10 holds the sensor element unit 5 such that a forward end portion of the sensor element unit 5 protrudes forward from the through hole 12 and a rear end portion of the sensor element unit 5 protrudes rearward from the through hole 12.

A ceramic holder 14 that is a tubular member surrounding the radial circumference of the sensor element unit 5, talc rings 15 and 16 that are layers of charged talc powder, and a ceramic sleeve 17 are stacked in this order inside the through hole 12 of the metallic shell 10 from the forward end side toward the rear end side.

A crimp packing 18 is disposed between the ceramic sleeve 17 and a rear end portion of the metallic shell 10. A metallic holder 19 is disposed between the ceramic holder 14 and the ledge 13 of the metallic shell 10. The talc ring 15 and the ceramic holder 14 are contained inside the metallic holder 19, and as a result of compressive charging of the material of the talc ring 15, the metallic holder 19 and the talc ring 15 are hermetically integrated together. A rear end portion of the metallic shell 10 is crimped so as to press the ceramic sleeve 17 toward the forward end side through the crimp packing 18. Since the material of the talc ring 16 is compressively charged into the metallic shell 10, the hermetic seal between the inner circumferential surface of the metallic shell 10 and the outer circumferential surface of the sensor element unit 5 is ensured.

An outer protector 21 with gas introduction holes and an inner protector 22 with gas introduction holes are disposed at a forward end portion of the metallic shell 10. The outer protector 21 and the inner protector 22 are each a tubular member formed from a metallic material such as stainless steel and having a closed forward end. The inner protector 22 covers a forward end portion of the sensor element unit 5 and is welded to the metallic shell 10, and the outer protector 21 covers the inner protector 22 and is welded to the metallic shell 10.

A forward end portion of an outer tube 31 formed into a tubular shape is welded to a rear outer circumference of the metallic shell 10. A grommet 32 is disposed in a rear end opening of the outer tube 31 so as to close the opening.

Lead wire insertion holes 33 into which lead wires 41 are inserted are formed in the grommet 32. The lead wires 41 are electrically connected to the electrode terminal portions 5A and 5B of the sensor element unit 5.

The separator 34 is a tubular member disposed rearward of the sensor element unit 5. A space formed inside the separator 34 is an insertion hole 35 passing through the separator 34 in the direction of the axial line O. A flange portion 36 protruding radially outward is formed on the outer surface of the separator 34.

A rear end portion of the sensor element unit 5 is inserted into the insertion hole 35 of the separator 34, and the electrode terminal portions 5A and 5B are disposed inside the separator 34.

A tubular metallic holding member 37 is disposed between the separator 34 and the outer tube 31. The holding member 37 is in contact with the flange portion 36 of the separator 34 and also with the inner surface of the outer tube 31 and thereby holds the separator 34 such that the separator 34 is fixed to the outer tube 31.

The connection terminals 38 are members disposed inside the insertion hole 35 of the separator 34 and are electrically conductive members that electrically connect the electrode terminal portions 5A and 5B of the sensor element unit 5 to their respective lead wires 41. In FIG. 1, only two connection terminals 38 are shown for the purpose of simplifying the drawing.

As shown in FIG. 2, the control section 3 of the multi-gas detection apparatus is electrically connected to an electronic controller 200 mounted on the present vehicle. The electronic controller 200 receives data representing the concentration of $NO_2$, the concentration of NOx, and the concentration of ammonia (hereinafter referred to as the concentration of $NH_3$) in exhaust gas that are computed by the control section 3. Then the electronic controller 200 performs processing for controlling the operating conditions of the internal combustion engine on the basis of the data received and also performs cleaning processing for NOx accumulated in the catalyst.

Figure 3:
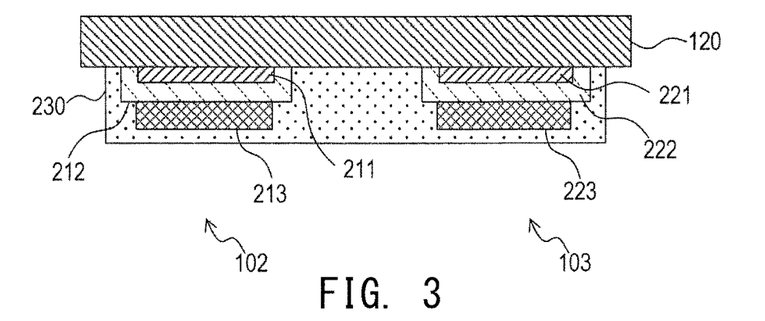
FIG. 3 is a cross-sectional view showing the structure of a first ammonia detection section 102 and second ammonia detection section 103.

The sensor element unit 5 includes the NOx detection section 101, the first ammonia detection section 102, and the second ammonia detection section 103. The second ammonia detection section 103 is not shown in FIG. 2 but is shown in FIG. 3. The first ammonia detection section 102 and the second ammonia detection section 103 are disposed in parallel at substantially the same position as a reference electrode 143 in the longitudinal direction of the NOx detection section 101 (i.e., the horizontal direction in FIG. 2) in such a manner that the first ammonia detection section 102 and the second ammonia detection section 103 are located at different positions in the width direction of the NOx detection section 101 (i.e., the direction perpendicular to the sheet on which FIG. 2 is depicted). Therefore, in FIG. 2, of the first ammonia detection section 102 and the second ammonia detection section 103, only the first ammonia detection section 102 is shown.

The NOx detection section 101 is formed by sequentially stacking an insulating layer 113, a ceramic layer 114, an insulating layer 115, a ceramic layer 116, an insulating layer 117, a ceramic layer 118, an insulating layer 119, and an insulating layer 120. The insulating layers 113, 115, 117, 119, and 120 and the ceramic layers 114, 116, and 118 are formed mainly of alumina.

The NOx detection section 101 includes a first measurement chamber 121 formed between the ceramic layer 114 and the ceramic layer 116. In the NOx detection section 101, the exhaust gas is introduced from the outside into the interior of the first measurement chamber 121 through a diffusion resistor 122 that is disposed between the ceramic layer 114 and the ceramic layer 116 so as to be adjacent to the first measurement chamber 121. The diffusion resistor 122 is formed of a porous material such as alumina.

The NOx detection section 101 further includes a first pumping cell 130. The first pumping cell 130 includes a solid electrolyte layer 131 and pumping electrodes 132 and 133.

The solid electrolyte layer 131 is formed mainly of zirconia having oxygen ion conductivity. A part of the ceramic layer 114 is removed from a region exposed to the first measurement chamber 121. Instead of the ceramic layer 114, the solid electrolyte layer 131 is embedded in the resulting space.

The pumping electrodes 132 and 133 are formed mainly of platinum. The pumping electrode 132 is disposed on a surface of the solid electrolyte layer 131, which surface is exposed to the first measurement chamber 121. The pumping electrode 133 is disposed on the solid electrolyte layer 131 on the side opposite the pumping electrode 132 with the solid electrolyte layer 131 sandwiched between the pumping electrodes 132 and 133. The insulating layer 113 is removed from a region in which the pumping electrode 133 is disposed and from a region around the pumping electrode 133, and the resulting space is filled with a porous material 134 instead of the insulating layer 113. The porous material 134 allows gas (e.g., oxygen) migration between the pumping electrode 133 and the outside.

The NOx detection section 101 further includes an oxygen concentration detection cell 140. The oxygen concentration detection cell 140 includes a solid electrolyte layer 141, a detection electrode 142, and the reference electrode 143.

The solid electrolyte layer 141 is formed mainly of zirconia having oxygen ion conductivity. A part of the ceramic layer 116 is removed from a region on the rear end side (i.e., the right side of FIG. 2) of the solid electrolyte layer 131. Instead of the ceramic layer 116, the solid electrolyte layer 141 is embedded in the resulting space.

The detection electrode 142 and the reference electrode 143 are formed mainly of platinum. The detection electrode 142 is disposed on a surface of the solid electrolyte layer 141, which surface is exposed to the first measurement chamber 121. The reference electrode 143 is disposed on the solid electrolyte layer 141 on the side opposite the detection electrode 142 with the solid electrolyte layer 141 sandwiched between the detection electrode 142 and the reference electrode 143.

The NOx detection section 101 includes a reference oxygen chamber 146. The reference oxygen chamber 146 is a through hole formed by removing the insulating layer 117 from a region in which the reference electrode 143 is disposed and from a region around the reference electrode 143.

The NOx detection section 101 includes a second measurement chamber 148 disposed downstream of the first measurement chamber 121. The second measurement chamber 148 is formed rearward of the detection electrode 142 and the reference electrode 143 so as to pass through the solid electrolyte layer 141 and the insulating layer 117. In the NOx detection section 101, the exhaust gas discharged from the first measurement chamber 121 is introduced into the second measurement chamber 148.

The NOx detection section 101 includes a second pumping cell 150. The second pumping cell 150 includes a solid electrolyte layer 151 and pumping electrodes 152 and 153.

The solid electrolyte layer 151 is formed mainly of zirconia having oxygen ion conductivity. The ceramic layer 118 is removed from a region exposed to the reference oxygen chamber 146 and the second measurement chamber 148 and a region around this exposed region. Instead of the ceramic layer 118, the solid electrolyte layer 151 is embedded in the resulting space.

The pumping electrodes 152 and 153 are formed mainly of platinum. The pumping electrode 152 is disposed on a surface of the solid electrolyte layer 151, which surface is exposed to the second measurement chamber 148. The pumping electrode 153 is disposed on the solid electrolyte layer 151 such that the pumping electrode 153 faces the reference electrode 143 with the reference oxygen chamber 146 therebetween. A porous material 147 is disposed inside the reference oxygen chamber 146 so as to cover the pumping electrode 153.

The NOx detection section 101 includes a heater 160. The heater 160 is a heat-generating resistor that is formed mainly of platinum and generates heat when energized and is disposed between the insulating layers 119 and 120.

The first ammonia detection section 102 is formed on the outer surface of the NOx detection section 101, more specifically on the insulating layer 120. The first ammonia detection section 102 is disposed at substantially the same position, with respect to the direction of the axial line O (i.e., the horizontal direction in FIG. 2), as the reference electrode 143 in the NOx detection section 101.

The first ammonia detection section 102 includes a first reference electrode 211 formed on the insulating layer 120, a first solid electrolyte body 212 covering the front and side surfaces of the first reference electrode 211, and a first detection electrode 213 formed on the front surface of the first solid electrolyte body 212. Similarly, as shown in FIG. 3, the second ammonia detection section 103 includes a second reference electrode 221 formed on the insulating layer 120, a second solid electrolyte body 222 covering the front and side surfaces of the second reference electrode 221, and a second detection electrode 223 formed on the front surface of the second solid electrolyte body 222.

The first reference electrode 211 and the second reference electrode 221 are formed mainly of platinum used as an electrode material and more specifically formed of a material containing Pt and zirconium oxide. The first solid electrolyte body 212 and the second solid electrolyte body 222 are formed of an oxygen ion-conductive material such as yttria-stabilized zirconia. The first detection electrode 213 and the second detection electrode 223 are formed mainly of gold used as an electrode material and more specifically formed of a material containing Au and zirconium oxide. The electrode materials of the first detection electrode 213 and the second detection electrode 223 are selected such that the first ammonia detection section 102 and the second ammonia detection section 103 differ from each other in terms of the ratio between the sensitivity to ammonia and the sensitivity to NOx.

The first ammonia detection section 102 and the second ammonia detection section 103 are covered with a porous protecting layer 230. The protecting layer 230 is configured to prevent adhesion of a poisoning material to the first detection electrode 213 and the second detection electrode 223 and to control the diffusion rate of ammonia flowing from the outside into the first ammonia detection section 102 and the second ammonia detection section 103. As described above, the first ammonia detection section 102 and the second ammonia detection section 103 function as mixed potential sensing sections.

As shown in FIG. 2, the control unit 3 includes a control circuit 180 and a microcomputer 190.

The control circuit 180 is an analog circuit disposed on a circuit board. The control circuit 180 includes an Ip1 drive circuit 181, a Vs detection circuit 182, a reference voltage comparison circuit 183, an Icp supply circuit 184, a Vp2 application circuit 185, an Ip2 detection circuit 186, a heater drive circuit 187, and an electromotive force detection circuit 188.

The pumping electrode 132, the detection electrode 142, and the pumping electrode 152 are connected to a reference potential. The pumping electrode 133 is connected to the Ip1 drive circuit 181. The reference electrode 143 is connected to the Vs detection circuit 182 and the Icp supply circuit 184. The pumping electrode 153 is connected to the Vp2 application circuit 185 and the Ip2 detection circuit 186. The heater 160 is connected to the heater drive circuit 187.

The Ip1 drive circuit 181 applies a voltage Vp1 between the pumping electrode 132 and the pumping electrode 133 to supply a first pumping current Ip1 and detects the supplied first pumping current Ip1.

The Vs detection circuit 182 detects the voltage Vs between the detection electrode 142 and the reference electrode 143 and outputs the detection result to the reference voltage comparison circuit 183.

The reference voltage comparison circuit 183 compares a reference voltage (e.g., 425 mV) with the output from the Vs detection circuit 182 (i.e., the voltage Vs) and outputs the comparison result to the Ip1 drive circuit 181. The Ip1 drive circuit 181 controls the direction and magnitude of the first pumping current Ip1 such that the voltage Vs becomes equal to the reference voltage to thereby adjust the concentration of oxygen in the first measurement chamber 121 to a prescribed value at which decomposition of NOx does not occur.

The Icp supply circuit 184 causes a weak current Icp to flow between the detection electrode 142 and the reference electrode 143. Oxygen is thereby fed from the first measurement chamber 121 to the reference oxygen chamber 146 through the solid electrolyte layer 141, and the concentration of oxygen in the reference oxygen chamber 146 is set to be a prescribed oxygen concentration serving as a reference.

The Vp2 application circuit 185 applies a constant voltage Vp2 (e.g., 450 mV) between the pumping electrode 152 and the pumping electrode 153. In the second measurement chamber 148, NOx is dissociated through the catalytic action of the pumping electrodes 152 and 153 of the second pumping cell 150. The oxygen ions obtained as a result of the dissociation migrate in the solid electrolyte layer 151 between the pumping electrode 152 and the pumping electrode 153, so that a second pumping current Ip2 flows. The Ip2 detection circuit 186 detects the second pumping current Ip2.

The heater drive circuit 187 applies a positive voltage for heater energization to one end of the heater 160, which is a heat-generating resistor, and applies a negative voltage for heater energization to the other end of the heater 160 to thereby drive the heater 160.

The electromotive force detection circuit 188 detects the electromotive force between the first reference electrode 211 and the first detection electrode 213 (hereinafter referred to as a first ammonia electromotive force) and the electromotive force between the second reference electrode 221 and the second detection electrode 223 (hereinafter referred to as a second ammonia electromotive force), and outputs signals representing the detection results to the microcomputer 190.

The microcomputer 190 includes a CPU 191, a ROM 192, a RAM 193, and a signal input/output unit 194. The CPU 191 executes programs stored in a non-transitory tangible recording medium to implement various functions of the microcomputer. In the present example, the ROM 192 corresponds to the non-transitory tangible recording medium in which the programs are stored. When one of the programs is executed, a method corresponding to the program is executed. The number of microcomputers included in the control unit 3 may be one or may be two or more. Part or all of the functions executed by the microcomputer 190 may be implemented by hardware using one or a plurality of ICs, etc.

The CPU 191 executes a process for controlling the sensor element unit 5 according to a program stored in the ROM 192. The signal input/output unit 194 is connected to the Ip1 drive circuit 181, the Vs detection circuit 182, the Ip2 detection circuit 186, the heater drive circuit 187, and the electromotive force detection circuit 188. The signal input/output unit 194 converts the voltage values of analog signals from the Ip1 drive circuit 181, the Vs detection circuit 182, the Ip2 detection circuit 186, and the electromotive force detection circuit 188 to digital data and outputs the digital data to the CPU 191.

The CPU 191 outputs a driving signal to the heater drive circuit 187 through the signal input/output unit 194 so as to control the electric power supplied to the heater 160 by means of pulse width modulation such that the heater 160 reaches a target temperature. To control the electric power supplied to the heater 160, any known method may be used. Specifically, the impedance of a cell (e.g., the oxygen concentration detection cell 140) included in the NOx detection section 101 is detected, and then the amount of the electric power supplied is controlled such that the impedance detected reaches a target value.

The CPU 191 reads various data from the ROM 192 and performs various computation processes on the basis of the value of the first pumping current Ip1, the value of the second pumping current Ip2, the value of the first ammonia electromotive force, and the value of the second ammonia electromotive force.

The ROM 192 stores a "first ammonia electromotive force—first ammonia concentration output relational expression," a "second ammonia electromotive force—second ammonia concentration output relational expression," a "first pumping current—oxygen concentration relational expression," a "second pumping current—NOx concentration output relational expression," a "first ammonia concentration output & second ammonia concentration output & oxygen concentration—corrected ammonia concentration relational expression," a "first ammonia concentration output & second ammonia concentration output & oxygen concentration—corrected $NO_2$ concentration relational expression," and an "NOx concentration output & corrected ammonia concentration & corrected $NO_2$ concentration—corrected NOx concentration relational expression."

The "first ammonia concentration output & second ammonia concentration output & oxygen concentration—corrected ammonia concentration relational expression" corresponds to correction expression (1) below. The "first ammonia concentration output & second ammonia concentration output & oxygen concentration—corrected $NO_2$ concentration relational expression" corresponds to correction expression (2) below. The "NOx concentration output & corrected ammonia concentration & corrected $NO_2$ concentration—corrected NOx concentration relational expression" corresponds to correction expression (3) below.

The various data may be set in the form of predetermined relational expressions as described above or may be set in other forms (for example, tables) so long as various gas concentrations can be calculated from the outputs of the sensor. Alternatively, they may be values obtained through the use of a model gas whose gas concentration is known.

The "first ammonia electromotive force—first ammonia concentration output relational expression" and the "second ammonia electromotive force—second ammonia concentration output relational expression" are expressions representing the relation between the ammonia electromotive forces outputted from the first ammonia detection section 102 and the second ammonia detection section 103 and the ammonia concentration outputs.

The "first pumping current—oxygen concentration relational expression" is an expression representing the relation between the first pumping current and the oxygen concentration (i.e., the $O_2$ concentration) in the exhaust gas. The "second pumping current—NOx concentration output relational expression" is an expression representing the relation between the second pumping current and the NOx concentration output.

The "first ammonia concentration output & second ammonia concentration output & oxygen concentration—corrected ammonia concentration relational expression" is an expression representing the relation between the first and second ammonia concentration outputs affected by the oxygen concentration, the ammonia concentration, and the $NO_2$ concentration and the corrected ammonia concentration from which the influences of the oxygen concentration and the $NO_2$ concentration have been removed. The "first ammonia concentration output & second ammonia concentration output & oxygen concentration—corrected $NO_2$ concentration relational expression" is an expression representing the relation between the first and second ammonia concentration outputs affected by the oxygen concentration, the ammonia concentration, and the $NO_2$ concentration and the corrected $NO_2$ concentration from which the influences of the oxygen concentration and the ammonia concentration have been removed. The "NOx concentration output & corrected ammonia concentration & corrected $NO_2$ concentration—corrected NOx concentration relational expression" is an expression representing the relation between the NOx concentration output affected by the ammonia concentration and the $NO_2$ concentration and the corrected NOx concentration from which the influences of the ammonia concentration and the $NO_2$ concentration have been removed.

A description will next be given of a computation process for determining the $NO_2$ concentration, the NOx concentration, and the ammonia concentration from the first pumping current Ip1, the second pumping current Ip2, the first ammonia electromotive force, and the second ammonia electromotive force. This computation process is executed by the CPU 191 of the microcomputer 190.

When the first pumping current Ip1, the second pumping current Ip2, the first ammonia electromotive force, and the second ammonia electromotive force are inputted, the CPU 191 performs a computation process for determining the oxygen concentration, the NOx concentration output, the first ammonia concentration output, and the second ammonia concentration output. Specifically, the CPU 191 calls the "first ammonia electromotive force—first ammonia concentration output relational expression," the "second ammonia electromotive force—second ammonia concentration output relational expression," the "first pumping current Ip1—oxygen concentration relational expression," and the "second pumping current Ip2—NOx concentration output relational expression" from the ROM 192 and then calculates the oxygen concentration and other concentration outputs using these relational expressions.

The "first ammonia electromotive force—first ammonia concentration output relational expression" and the "second ammonia electromotive force—second ammonia concentration output relational expression" are set such that, over the entire possible range of the ammonia electromotive forces outputted from the first and second ammonia detection sections 102 and 103 in their use environment, an approximately linear relation is present between each of the ammonia concentration outputs from the first and second ammonia detection sections 102 and 103 and the ammonia concentration in the measurement gas. Since these conversion expressions are used for conversion, in the correction expressions below, calculation which utilizes changes in gradient and offset is possible.

After the oxygen concentration, the NOx concentration output, the first ammonia concentration output, and the second ammonia concentration output are determined, the CPU 191 performs computations using the correction expressions described below to determine the ammonia concentration, $NO_2$ concentration, and NOx concentration in the exhaust gas.

$$x=F(A,B,D)=(eA-c)*(jB-h-fA+d)/(eA-c-iB+g)+fA-d \quad \text{Correction expression (1):}$$

$$y=F'(A,B,D)=(jB-h-fA+d)/(eA-c-iB+g) \quad \text{Correction expression (2):}$$

$$z=C-ax+by \quad \text{Correction expression (3):}$$

In these correction expressions, x represents the ammonia concentration, y represents the $NO_2$ concentration, and z represents the NOx concentration. A represents the first ammonia concentration output, B represents the second ammonia concentration output, C represents the NOx concentration output, and D represents the oxygen concentration. F in the correction expression (1) represents that x is a function of A, B, and D, and F' in the correction expression (2) represents that y is a function of A, B, and D. a and b are correction coefficients, and c, d, e, f, g, h, and j are coefficients calculated using the oxygen concentration D (i.e., coefficients determined by D).

The CPU 191 determines the ammonia concentration, the $NO_2$ concentration, and the NOx concentration in the exhaust gas by substituting the first ammonia concentration output, the second ammonia concentration output, the NOx concentration output, and the oxygen concentration into the above-described correction expressions (1) to (3).

The correction expressions (1) and (2) are determined on the basis of the characteristics of the first and second ammonia detection sections 102 and 103, and the correction expression (3) is determined on the basis of the characteristics of the NOx detection section 101. The correction expressions (1) to (3) are merely examples, and other correction expressions, coefficients, etc. may be appropriately used in accordance with the characteristics of gas detection.

The microcomputer 190 in the control unit 3 executes gas concentration computation processing and gas leakage diagnosing processing. After the electric power is supplied to the heater 160 and the sensor element unit 5 is heated to its activation temperature by the heat generated by the heater 160, each of the gas concentration computation processing and the gas leakage diagnosing processing is executed every time an execution period elapses. In the present embodiment, the execution period is 50 ms.

Figure 4:
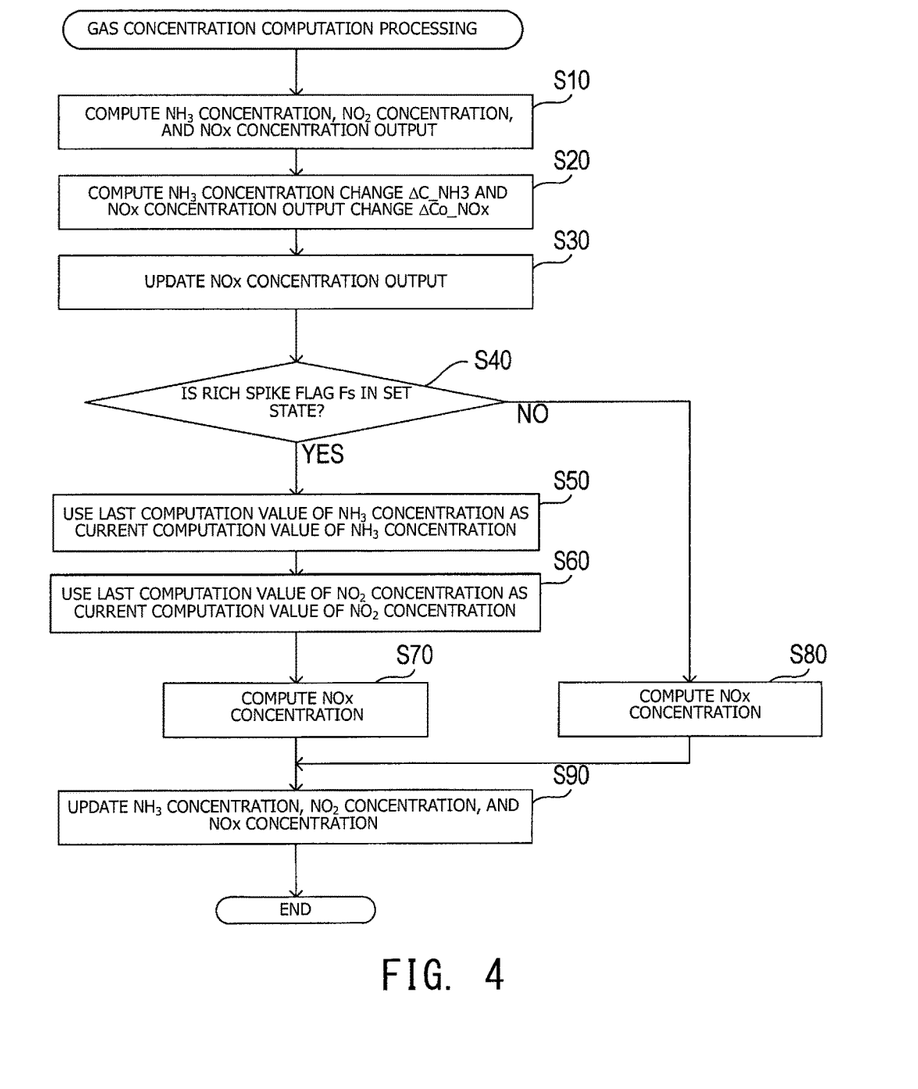
FIG. 4 is a flowchart showing gas concentration computation processing.

The steps of the gas concentration computation processing will be described.

As shown in FIG. 4, when the gas concentration computation processing is executed, in S10, the CPU 191 of the microcomputer 190 first acquires the results of detection of the first pumping current Ip1, the second pumping current Ip2, the first ammonia electromotive force, and the second ammonia electromotive force from the control circuit 180 and performs the above-described computations to compute the ammonia concentration, the $NO_2$ concentration, and the NOx concentration output. The NOx concentration output is a value obtained from a "second pumping current Ip2–NOx concentration output relational expression." In S10, the result of the computation of the ammonia concentration is stored in a storage area for computed ammonia concentration C_NH3_CAL provided in the RAM 193. In S10, the result of the computation of the $NO_2$ concentration is stored in a storage area for computed $NO_2$ concentration C_NO2_CAL provided in the RAM 193. In S10, the result of the computation of the NOx concentration output is stored in a storage area for computed NOx concentration output Co_NOx_CAL provided in the RAM 193.

Next, in S20, the CPU 191 computes the value of ammonia concentration change ΔC_NH3 and the value of NOx concentration output change ΔCo_NOx. Specifically, through use of the value stored in a memory area for ammonia concentration C_NH3 provided in the RAM 193, the CPU 191 computes the value of ammonia concentration change ΔC_NH3 in accordance with formula (1) below. Also, through use of the value stored in a memory area for NOx concentration output four periods ago Co_NOx_4 (described later) provided in the RAM 193, the CPU 191 computes the value of NOx concentration output change ΔCo_NOx in accordance with formula (2) below.

$$\Delta C\_NH3 = C\_NH3\_CAL - C\_NH3 \quad (1)$$

$$\Delta Co\_NOx = Co\_NOx\_CAL - Co\_NOx\_4 \quad (2)$$

Ammonia concentration C_NH3 represents the latest ammonia concentration before the value of computed ammonia concentration C_NH3_CAL is computed.

A memory area for $NO_2$ concentration C_NO2 is provided in the RAM 193. $NO_2$ concentration C_NO2 represents the latest $NO_2$ concentration before the value of computed $NO_2$ concentration C_NO2_CAL is computed.

Respective memory areas for NOx concentration output Co_NOx, NOx concentration output one period ago Co_NOx_1, NOx concentration output two periods ago Co_NOx_2, NOx concentration output three periods ago Co_NOx_3, and NOx concentration output four periods ago Co_NOx_4 are provided in the RAM 193.

NOx concentration output Co_NOx represents the latest NOx concentration output before the value of computed NOx concentration output Co_NOx_CAL is computed.

NOx concentration output one period ago Co_NOx_1 represents the NOx concentration output computed one execution period before (i.e., 50 ms before) the computation of the value of NOx concentration output Co_NOx. NOx concentration output two periods ago Co_NOx_2 represents the NOx concentration output computed two execution periods before (i.e., 100 ms before) the computation of the value of NOx concentration output Co_NOx. NOx concentration output three periods ago Co_NOx_3 represents the NOx concentration output computed three execution periods before (i.e., 150 ms before) the computation of the value of NOx concentration output Co_NOx.

NOx concentration output four periods ago Co_NOx_4 represents the NOx concentration output computed four execution periods before (i.e., 200 ms before) the computation of the value of NOx concentration output Co_NOx. Namely, NOx concentration output four periods ago Co_NOx_4 represents the NOx concentration output five execution periods before (i.e., 250 ms before) the computation of the value of computed NOx concentration output Co_NOx_CAL.

In S30, the CPU 191 reads the value stored in the memory area for NOx concentration output three periods ago Co_NOx_3 and stores it in the memory area for NOx concentration output four periods ago Co_NOx_4. The CPU 191 reads the value stored in the memory area for NOx concentration output two periods ago Co_NOx_2 and stores it in the memory area for NOx concentration output three periods ago Co_NOx_3. The CPU 191 reads the value stored in the memory area for NOx concentration output one period ago Co_NOx_1 and stores it in the memory area for NOx concentration output two periods ago Co_NOx_2. The CPU 191 reads the value stored in the memory area for NOx concentration output Co_NOx and stores it in the memory area for NOx concentration output one period ago Co_NOx_1. The CPU 191 reads the value stored in the memory area for computed NOx concentration output Co_NOx_CAL and stores it in the memory area for NOx concentration output Co_NOx.

In S40, the CPU 191 determines whether or not a rich spike flag Fs provided in the RAM 193 is in a set state. The rich spike flag Fs is set or cleared in the gas leakage diagnosing processing described later.

If the rich spike flag Fs is in the set state (YES in S40), in S50, the CPU 191 reads the value stored in the memory area for ammonia concentration C_NH3 and stores it in the memory area for computed ammonia concentration C_NH3_CAL. Specifically, the last computation value of the ammonia concentration is used as the current computation value of the ammonia concentration.

In S60, the CPU 191 reads the value stored in the memory area for $NO_2$ concentration C_NO2 and stores it in the memory area for computed $NO_2$ concentration C_NO2 CAL. Specifically, the last computation value of the $NO_2$ concentration is used as the current computation value of the $NO_2$ concentration.

In S70, through use of the value currently stored in the memory area for NOx concentration output Co_NOx, the value currently stored in the memory area for ammonia concentration C_NH3, and the value currently stored in the memory area for $NO_2$ concentration C_NO2, the CPU 191 computes the NOx concentration in accordance with the correction expression (3) above. Namely, the CPU 191 computes the NOx concentration using the last computation value of the ammonia concentration and the last computation value of the $NO_2$ concentration. The CPU 191 stores the result of the computation of the NOx concentration in the memory area for computed NOx concentration C_NOx_CAL provided in the RAM 193, and proceeds to S90.

If the rich spike flag Fs is not in the set state, through use of the ammonia concentration, $NO_2$ concentration, and NOx concentration output computed in S10, the CPU 191 computes the NOx concentration in accordance with the above-described correction expression (3) in S80. The CPU 191 stores the result of the computation of the NOx concentration in the memory area for computed NOx concentration C_NOx_CAL provided in the RAM 193, and proceeds to S90.

In S90, the CPU 191 updates the value of ammonia concentration C_NH3, the value of $NO_2$ concentration C_NO2, and the value of NOx concentration C_NOx, and ends the current execution of the gas concentration computation processing. Specifically, the CPU 191 reads the value stored in the memory area for computed ammonia concentration C_NH3_CAL and stores it in the memory area for ammonia concentration C_NH3. The CPU 191 reads the value stored in the memory area for computed $NO_2$ concentration C_NO2 CAL and stores it in the memory area for $NO_2$ concentration C_NO2. The CPU 191 reads the value stored in the memory area for computed NOx concentration C_NOx_CAL and stores it in the memory area for NOx concentration C_NOx.

Figure 5:
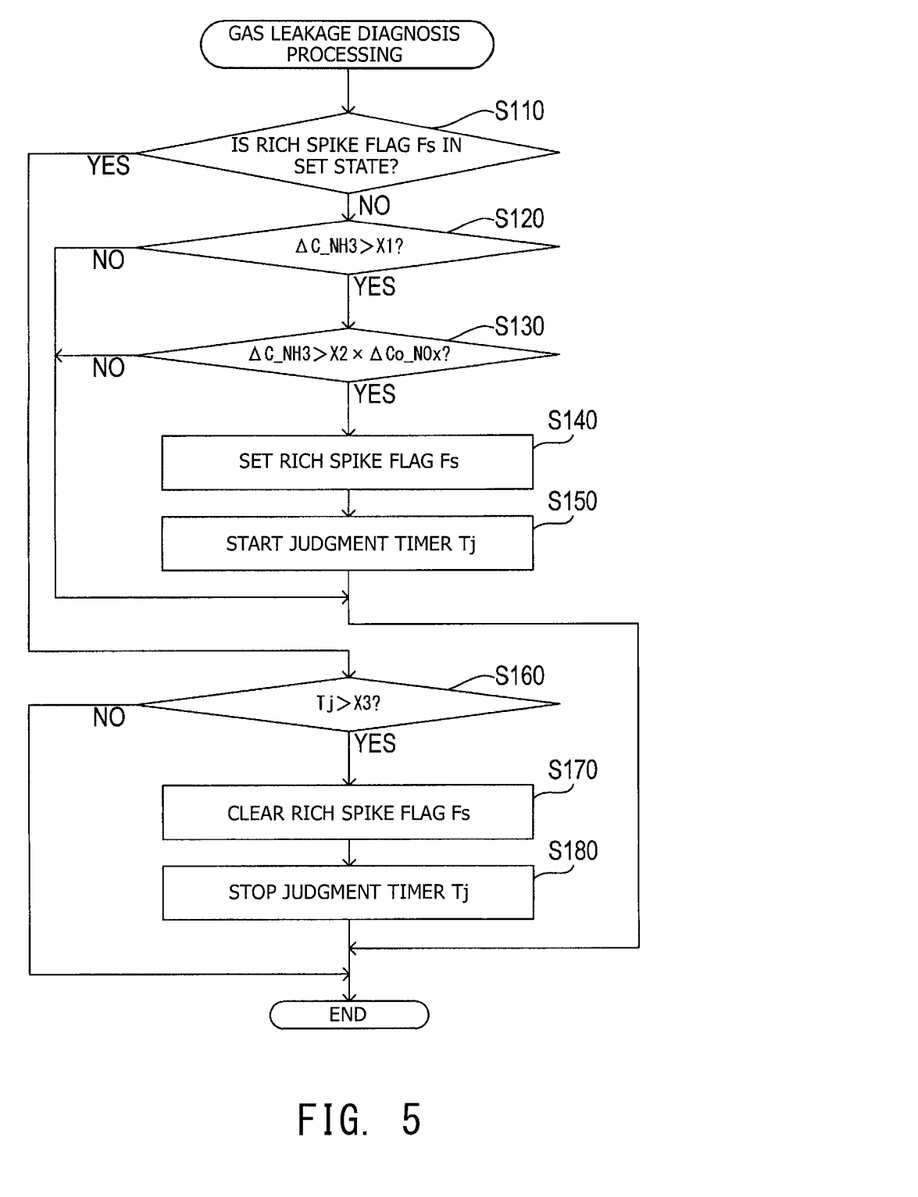
FIG. 5 is a flowchart showing gas leakage diagnosing processing.

Next, the steps of the gas leakage diagnosing processing will be described.

As shown in FIG. 5, when the gas leakage diagnosing processing is executed, the CPU 191 of the microcomputer 190 determines in S110 whether or not the rich spike flag Fs is in the set state. If the rich spike flag Fs is not in the set state, the CPU 191 determines in S120 whether or not the value of ammonia concentration change ΔC_NH3 is larger than a preset diagnosis start determination value X1.

If the value of ammonia concentration change ΔC_NH3 is equal to or less than the diagnosis start determination value X1, the CPU 191 ends the current execution of the gas leakage diagnosing processing. If the value of ammonia concentration change ΔC_NH3 is larger than the diagnosis start determination value X1, the CPU 191 determines in S130 whether or not the value of ammonia concentration change ΔC_NH3 is larger than the product of a preset diagnosis start determination coefficient X2 and the NOx concentration output change ΔCo_NOx. The diagnosis start determination coefficient X2 is set to a value larger than 1.

If the value of ammonia concentration change ΔC_NH3 is equal to or less than the product of the diagnosis start determination coefficient X2 and the NOx concentration output change ΔCo_NOx, the CPU 191 ends the current execution of the gas leakage diagnosing processing. If the value of ammonia concentration change ΔC_NH3 is larger than the product of the diagnosis start determination coefficient X2 and the NOx concentration output change ΔCo_NOx, the CPU 191 sets the rich spike flag Fs in S140. Further, in S150, the CPU 191 starts a judgment timer Tj provided in the RAM 193, and ends the current execution of the gas leakage diagnosing processing. The judgment timer Tj is incremented, for example, every 10 ms. After the judgment timer Tj is started, its value is incremented from 0 (i.e., one is added).

If the CPU 191 determines in S110 that the rich spike flag Fs is in the set state, the CPU 191 determines in S160 whether or not the value of the judgment timer Tj is larger than a preset continuation determination value X3. In the present embodiment, the continuation determination value X3 is a value corresponding to, for example, 2 seconds.

If the value of the judgment timer Tj is equal to or less than the continuation determination value X3, the CPU 191 ends the current execution of the gas leakage diagnosing processing. If the value of the judgment timer Tj is larger than the continuation determination value X3, the CPU 191 clears (resets) the rich spike flag Fs in S170. Further, the CPU 191 stops the increment of the judgment timer Tj in S180, and ends the current execution of the gas leakage diagnosing processing.

Figure 6:
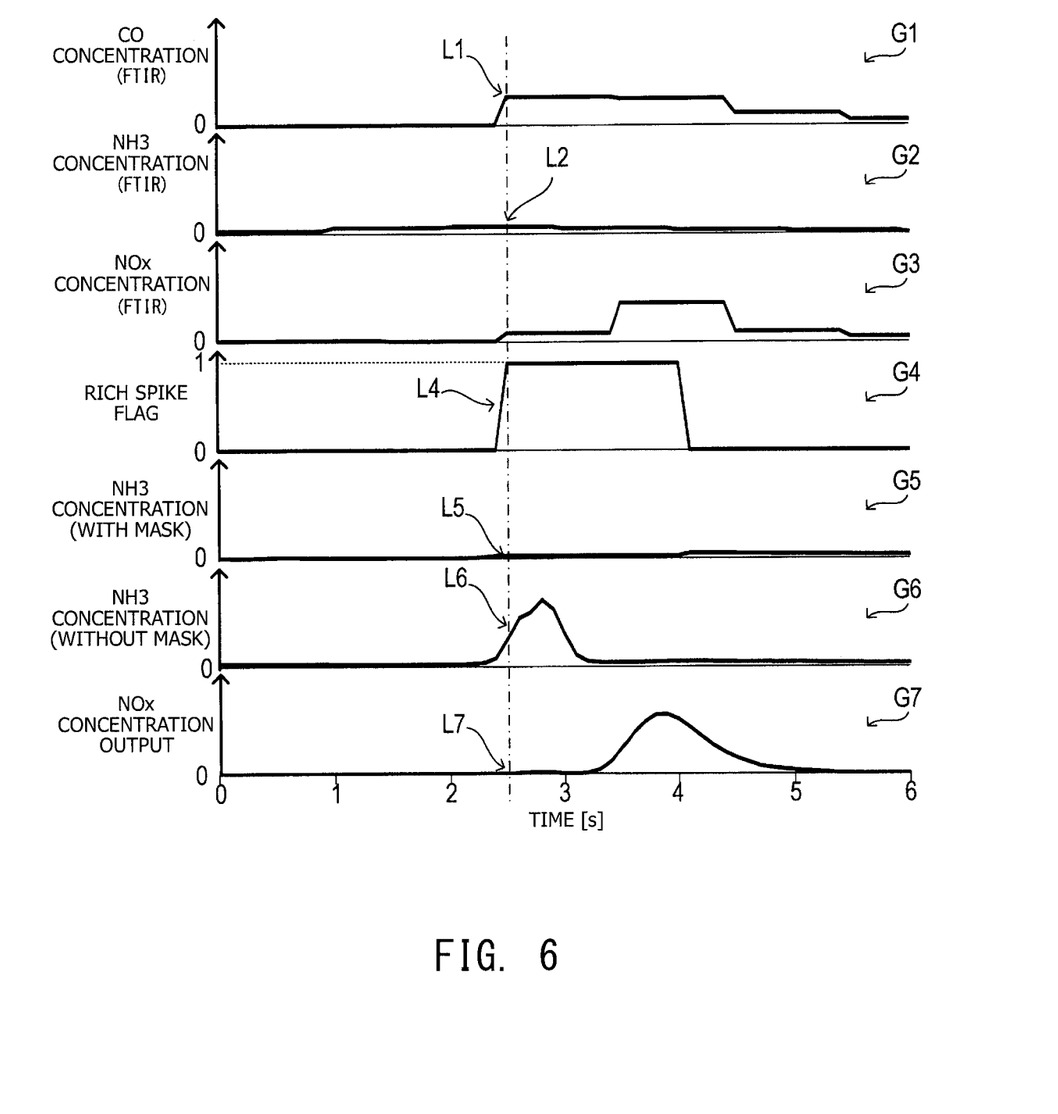
FIG. 6 is a graphs showing changes in ammonia concentration, NOx concentration, CO concentration, rich spike flag, etc. with time.

Graph G1 in FIG. 6 shows changes in the concentration of carbon monoxide contained in the exhaust gas with time. Graph G2 in FIG. 6 shows changes in the concentration of ammonia contained in the exhaust gas with time. Graph G3 in FIG. 6 shows changes in the concentration of nitrogen oxide contained in the exhaust gas with time. Graphs G1, G2, and G3 show the results of measurement obtained using a Fourier transform infrared spectrometer.

Graph G4 in FIG. 6 shows changes in the rich spike flag Fs with time. Graph G5 in FIG. 6 shows changes in the value of ammonia concentration C_NH3 with time when the gas leakage diagnosing processing is used. Graph G6 in FIG. 6 shows changes in the value of ammonia concentration C_NH3 with time when the gas leakage diagnosing processing is not used. Graph G7 in FIG. 6 shows changes in the value of NOx concentration output Co_NOx with time.

As shown by arrow L1 in graph G1, a steep rise in the concentration of carbon monoxide due to a rich spike occurs at around 2.6 seconds. As shown by arrow L2 in graph G2, almost no change in the ammonia concentration occurs at around 2.6 seconds. However, as shown by arrow L6 in graph G6, a steep rise in the ammonia concentration C_NH3 occurs at around 2.6 seconds despite that, as shown by arrow L2 in graph G2, almost no change in the concentration of ammonia contained in the exhaust gas occurs at around 2.6 seconds. As shown by arrow L7 in graph G7, almost no change in the value of NOx concentration output Co_NOx occurs at around 2.6 seconds.

Therefore, as shown by arrow L4 in graph G4, the rich spike flag Fs is set at around 2.6 seconds. As shown by arrow L5 in graph G5, when the gas leakage diagnosing processing is used, almost no change in the value of ammonia concentration C_NH3 occurs at around 2.6 seconds.

The microcomputer 190 configured as described above computes the concentration of ammonia contained in exhaust gas.

The microcomputer 190 acquires the first ammonia electromotive force from the first ammonia detection section 102, acquires the second ammonia electromotive force from the second ammonia detection section 103, and computes, as computed ammonia concentration C_NH3_CAL, the concentration of ammonia contained in the exhaust gas based on the first ammonia electromotive force and the second ammonia electromotive force.

The first ammonia detection section 102 and the second ammonia detection section 103 output the first ammonia electromotive force and the second ammonia electromotive force, respectively, each of which varies according to both the concentration of ammonia contained in the exhaust gas and the concentration of the flammable gas contained in the exhaust gas. In the present embodiment, the flammable gas includes carbon monoxide (i.e., CO) and hydro carbon (i.e., HC).

The microcomputer 190 acquires the second pumping current Ip2 from the NOx detection section 101 and computes, as computed NOx concentration C_NOx_CAL, the concentration of NOx based on the second pumping current Ip2. The NOx detection section 101 outputs the second pumping current Ip2 which varies according to the concentration of NOx contained in the exhaust gas and also varies according to the concentration of ammonia contained in the exhaust gas. The NOx detection section 101 has characteristics that the second pumping current Ip2 does not vary according to the concentration of the flammable gas.

The microcomputer 190 determines whether or not the exhaust gas contains the flammable gas based on at least the first and second ammonia electromotive forces and the second pumping current Ip2. In the present embodiment, when the value of ammonia concentration change ΔC_NH3 is greater than the diagnosis start determination value X1 and the value of ammonia concentration change ΔC_NH3 is greater than the product of the diagnosis start determination coefficient X2 and the value of NOx concentration output change ΔCo_NOx, the microcomputer 190 determines that the exhaust gas contains the flammable gas and sets the rich spike flag Fs.

In the case where the microcomputer 190 determines that the exhaust gas does not contain the flammable gas, the microcomputer 190 sets (stores), as the value of ammonia concentration C_NH3, the value of computed ammonia concentration C_NH3_CAL computed through use of the ammonia concentration, $NO_2$ concentration, and NOx concentration output computed in S10.

In the case where the microcomputer 190 determines that the exhaust gas contains the flammable gas, the microcomputer 190 prohibits the operation of setting (storing), as the value of ammonia concentration C_NH3, the value of computed ammonia concentration C_NH3_CAL computed through use of the ammonia concentration, $NO_2$ concentration, and NOx concentration output computed in S10.

As described above, the microcomputer 190 can determine whether or not the exhaust gas contains the flammable gas. When a rich spike occurs, the exhaust gas contains the flammable gas. Therefore, even when the concentration of oxygen contained in the exhaust gas does not decrease sharply, the microcomputer 190 can detect the rich spike, whereby the accuracy in detecting the rich spike can be improved.

In the case where the microcomputer 190 determines that the exhaust gas contains the flammable gas, the microcomputer 190 prohibits the operation of setting (storing), as the value of ammonia concentration C_NH3, the value of computed ammonia concentration C_NH3_CAL computed through use of the ammonia concentration, $NO_2$ concentration, and NOx concentration output computed in S10. Therefore, the microcomputer 190 can prevent a reduction in the accuracy of computation of the ammonia concentration when a rich spike occurs.

When the value of ammonia concentration change ΔC_NH3 is greater than the diagnosis start determination value X1, the microcomputer 190 determines whether or not the exhaust gas contains the flammable gas. As a result, it is possible to prevent occurrence of a situation in which the determination as to whether or not the exhaust gas contains the flammable gas is performed even when the value of computed ammonia concentration C_NH3_CAL varies slightly due to noise. Thus, the processing load of the microcomputer 190 can be reduced.

The NOx detection section 101 detects NOx and outputs the second pumping current Ip2 which varies according to the concentration of ammonia contained in the exhaust gas. As a result, the microcomputer 190 can be used for computation of the concentration of NOx in the system for cleaning NOx contained in the exhaust gas discharged from the internal combustion engine.

The microcomputer 190 determines that the exhaust gas contains the flammable gas in the case where the value of ammonia concentration change ΔC_NH3 is greater than the product of the diagnosis start determination coefficient X2 and the value of NOx concentration output change ΔCo_NOx. As a result, as compared with the case where an absolute value is used, the influences of the concentrations of ammonia and the specific gas present as an atmospheric reference can be reduced, whereby more accurate determination becomes possible. Also, the microcomputer 190 can determine whether or not the exhaust gas contains the flammable gas by a simple method of comparing the value of ammonia concentration change ΔC_NH3 with the product of the value of NOx concentration output change ΔCo_NOx and the diagnosis start determination coefficient X2. Therefore, the processing load of the microcomputer 190 can be reduced.

In the present embodiment, the time interval of computation of ammonia concentration change ΔC_NH3 is 50 ms and the time interval of computation of NOx concentration output change ΔCo_NOx is 250 ms. Namely, the time interval of computation of NOx concentration output change ΔCo_NOx differs from the time interval of computation of ammonia concentration change ΔC_NH3 and is longer than the time interval of computation of ammonia concentration change ΔC_NH3. As a result, the microcomputer 190 can prevent occurrence of a situation in which the magnitude of NOx concentration output change ΔCo_NOx which corresponds to a change in the NOx concentration in the exhaust gas is computed such that the computed magnitude is smaller than the actual magnitude.

The NOx detection section 101, the first ammonia detection section 102, and the second ammonia detection section 103 are configured as the integral sensor element unit 5. As a result, the microcomputer 190 can detect the ammonia concentration and the NOx concentration in regions of the exhaust gas which are approximately the same.

In the present embodiment, the determination as to whether the exhaust gas contains the flammable gas is made through use of the value of ammonia concentration change ΔC_NH3. However, the determination may be made through use of at least one of the first and second ammonia concentration outputs as is or through use of at least one of the first and second ammonia electromotive forces as is. More accurate determination can be made through use of the ammonia concentration obtained by the correction expression (1) as in the present embodiment, because the ammonia concentration obtained by the correction expression (1) is a corrected value. Therefore, use of the ammonia concentration obtained by the correction expression (1) is desirable. In the present embodiment, the determination as to whether or not the exhaust gas contains the flammable gas is made through use of the change in the NOx concentration output. However, the second pumping current Ip2 may be used as is. Notably, the NOx concentration obtained by the correction expression (3) is not preferred, because the NOx concentration obtained by the correction expression (3) is a value corrected by the ammonia concentration output affected by the flammable gas.

In the above-described embodiment, the microcomputer 190 is an example of the concentration computation apparatus; S10 represents the first computation section; S80 represents the second computation section; S120 and S130 represent the flammable gas determination section; S90 represents the concentration setting section; and S50 represents the setting prohibition section.

The first ammonia detection section 102 and the second ammonia detection section 103 are examples of the first detection section; and the NOx detection section 101 is an example of the second detection section.

The exhaust gas is an example of the measurement gas; the first and second ammonia electromotive forces are examples of the first concentration signal; the value of computed ammonia concentration C_NH3_CAL is an example of the first computed concentration; NOx is an example of the specific gas; the second pumping current Ip2 is an example of the second concentration signal; the value of computed NOx concentration C_NOx_CAL is an example of the second computed concentration; and the value of ammonia concentration C_NH3 is an example of the latest ammonia concentration.

The diagnosis start determination value X1 is an example of the start determination value; the computed ammonia concentration C_NH3_CAL is an example of the first concentration parameter; and the computed NOx concentration output Co_NOx_CAL is an example of the second concentration parameter.

The value of ammonia concentration change ΔC_NH3 is an example of the change in the first concentration parameter; the value of NOx concentration output change ΔCo_NOx is an example of the change in the second concentration parameter; and the multi-gas sensor 2 is an example of the integral gas sensor.

While one embodiment of the present disclosure has been described, the present disclosure is not limited to the embodiment. The present disclosure can be implemented in various forms.

For example, in the above embodiment, the NOx detection section 101 and the ammonia detection sections 102 and 103 are used to determine whether or not the exhaust gas contains the flammable gas. However, the present disclosure is not limited to the determination using the NOx detection section and the ammonia detection sections. Instead of the NOx detection section, a flammable gas detection section that outputs a concentration signal that varies according to the concentration of the flammable gas and does not vary according to the concentration of ammonia may be used. In this case, if the output value of the concentration signal outputted from the flammable gas detection section is larger, the exhaust gas can be determined to contain the flammable gas.

In the above embodiments, if the exhaust gas is determined to contain the flammable gas, the value of ammonia concentration C_NH3 is not updated, and the last value is used. However, the value of ammonia concentration C_NH3 may be set to 0 or set to a preset prescribed value.

A plurality of functions included in a single component in the above-described embodiments may be distributed to a plurality of components, or functions of a plurality of components may be integrated into one component. Part of the configuration in each of the above-described embodiments may be omitted. At least part of the configuration in each of the above-described embodiments may be added to the configuration of another embodiment or may replace the configuration of another embodiment. Any embodiments included in the technical ideas specified by the wording of the claims are defined as embodiments of the present disclosure.

The present disclosure can be implemented as various forms such as the microcomputer 190 described above and as a system including the microcomputer 190 as a component, a program that causes the microcomputer 190 to function as a computer, a non-transitory tangible recording medium, e.g., a semiconductor memory, in which the program is stored, and a concentration computation method.

DESCRIPTION OF REFERENCE NUMERALS

2 . . . multi-gas sensor, 3 . . . control section, 101 . . . NOx detection section, 102 . . . first ammonia detection section, 103 . . . second ammonia detection section, 190 . . . microcomputer.

The invention claimed is:

1. A concentration computation apparatus for computing a concentration of ammonia contained in a measurement gas, the apparatus comprising:
a first computation section configured to acquire a first concentration signal which is output from a first detection section and to compute a first computed concentration, which is the concentration of ammonia contained in the measurement gas, based on the first concentration signal, whose value varies with both the concentration of ammonia contained in the measurement gas and the concentration of a flammable gas contained in the measurement gas;
a second computation section configured to acquire a second concentration signal which is output from a second detection section, and to compute a second computed concentration, which is a concentration of a specific gas other than ammonia, based on the second concentration signal, whose value varies with the concentration of the specific gas and the flammable gas contained in the measurement gas, and also varies with one of the concentration of ammonia contained in the measurement gas and the concentration of the flammable gas contained in the measurement gas;
a flammable gas determination section configured to determine whether or not the measurement gas contains the flammable gas based on at least the first concentration signal and the second concentration signal;
a concentration setting section configured to set the first computed concentration as a latest ammonia concentration when the flammable gas determination section determines that the measurement gas does not contain the flammable gas; and
a setting prohibition section configured to prohibit the concentration setting section from setting the first computed concentration as the latest ammonia concentration when the flammable gas determination section determines that the measurement gas contains the flammable gas.

2. The concentration computation apparatus according to claim 1, wherein the flammable gas determination section determines whether or not the measurement gas contains the flammable gas when a change in the first computed concentration during a predetermined first time interval is greater than a predetermined start determination value.

3. The concentration computation apparatus according to claim 1, wherein the second detection section detects nitrogen oxide as the specific gas and outputs the second concentration signal whose value varies with the concentration of ammonia contained in the measurement gas.

4. The concentration computation apparatus according to claim 1, wherein the flammable gas determination section determines whether or not the measurement gas contains the flammable gas through use of a predetermined first concentration parameter to have a positive correlation with the output value of the first concentration signal and a predetermined second concentration parameter to have a positive correlation with the output value of the second concentration signal, wherein
the flammable gas determination section determines that the measurement gas contains the flammable gas when a change in the first concentration parameter in a predetermined first time interval is greater than a change in the second concentration parameter in a predetermined second time interval.

5. The concentration computation apparatus according to claim 4, wherein the second time interval differs from the first time interval.

6. The concentration computation apparatus according to claim 1, further comprising an integral gas sensor that contains the first detection section and the second detection section.

* * * * *